United States Patent [19]

Hower

[11] Patent Number: 4,618,986

[45] Date of Patent: Oct. 21, 1986

[54] ELECTRONIC STETHOSCOPE

[75] Inventor: Larry H. Hower, New York, N.Y.

[73] Assignee: The Hart Group, Dallas, Tex.

[21] Appl. No.: 549,195

[22] Filed: Nov. 4, 1983

Related U.S. Application Data

[63] Continuation-in-part of Ser. No. 480,062, Mar. 29, 1983.

[51] Int. Cl.[4] ............................................... A61B 5/02
[52] U.S. Cl. ...................................... 381/67; 128/715
[58] Field of Search .......................... 381/67; 128/715

[56] References Cited

U.S. PATENT DOCUMENTS

| 3,160,708 | 12/1964 | Andries ................................. | 381/67 |
| 3,247,324 | 4/1966 | Cefaly ................................... | 381/67 |
| 3,539,724 | 11/1970 | Keesee .................................. | 381/67 |
| 3,989,895 | 11/1976 | O'Daniel .............................. | 381/67 |
| 4,071,694 | 1/1978 | Pfeiffer ................................. | 381/67 |
| 4,254,302 | 3/1981 | Walshe .................................. | 381/67 |
| 4,377,727 | 3/1983 | Schwalbach ......................... | 128/715 |
| 4,438,772 | 3/1984 | Slavin .................................. | 128/715 |
| 4,534,058 | 8/1985 | Hower .................................. | 381/67 |

FOREIGN PATENT DOCUMENTS 963230 7/1950 France .................................. 381/67

*Primary Examiner*—Gene Z. Rubinson
*Assistant Examiner*—L. C. Schroeder
*Attorney, Agent, or Firm*—Hubbard, Thurman, Turner & Tucker

[57] ABSTRACT

An electronic stethoscope is disclosed having a palm sized electronic component case with operating switches provided on opposite sides of the case for ease of operation. The stethoscope includes a pickup head coupled to an electronic microphone by means of a flexible tubular acoustic member. A battery powered amplifier and filter circuit is provided within the component case and the amplified and filtered output of the microphone is coupled to a miniature speaker sealed within an airtight container within the case. A rotatable tubular member having radial apertures therein is coupled through the sealed container and out each side of the component case. A binaural headpiece is acoustically coupled to each end of the rotatable member and is thus free to rotate with respect to the case, allowing the stethoscope to fold for storage. In a preferred embodiment of the present invention, electronic timing means are provided for automatically removing electrical power from than amplifier circuit after a predetermined period of time and for generating an audible tone at preselected intervals for pulse rate measurement.

8 Claims, 3 Drawing Figures

ELECTRONIC STETHOSCOPE

CROSS-REFERENCE TO RELATED APPLICATIONS

This application is a continuation-in-part of U.S. patent application Ser. No. 480,062, filed Mar. 29, 1983.

BACKGROUND OF THE INVENTION

This invention relates to stethoscopes in general and in particular to stethoscopes including electronic amplification circuitry. Still more particularly, this invention relates to improved electronic stethoscopes having enhanced noise rejection characteristics and automatic power conservation circuitry and which are designed to resemble simple acoustic stethoscopes in size and convenience.

Both electronic and acoustic stethoscopes and combinations of these two are well known in the art. One example of an electronic stethoscope is described in U.S. Pat. No. 3,247,324. That stethoscope includes a pickup head which is acoustically coupled, by means of a flexible conduit, to a microphone. The signals picked up by that microphone are then amplified and provided to a speaker which is acoustically coupled to a conventional binaural headpiece by means of flexible conduits. The stethoscope disclosed in U.S. Pat. No. 3,247,324 also permits direct acoustical connection between the pickup head and the binaural headpiece.

Electronic stethoscopes known in the prior art have not been generally accepted by medical practitioners due to several problems which exist in those designs. Typically, these known devices have been bulky and difficult to utilize, carry or store. Further, known electronic stethoscopes have suffered from reliability problems due to battery problems and interference due to background high frequency interference from fluorescent light fixtures or other sources. Clearly, there has existed a need for an electronic stethoscope which is physically similar to acoustic stethoscopes in size and convenience and which is not subject to the vagaries of known circuitry.

SUMMARY OF THE INVENTION

It is therefore one object of the present invention to provide an improved electronic stethoscope.

It is another object of the present invention to provide an improved electronic stethoscope which folds and stores in the manner of an acoustic stethoscope.

It is yet another object of the present invention to provide an improved electronic stethoscope which includes filter circuitry for enhancing selected frequency bands.

It is another object of the present invention to provide an improved electronic stethoscope which includes circuitry of automatically removing electrical power from the device after a selected period of time has elapsed to prevent excessive battery drain.

It is yet another object of the present invention to provide an improved electronic stethoscope which includes circuitry for generating periodic audible pulses or tones for utilization in pulse rate measurements.

The foregoing objects are achieved as is now described. The electronic stethoscope of the present invention includes a palm sized electronic component case with operating switches provided on opposite sides of the case for ease of operation. The stethoscope includes a pickup head coupled to an electronic microphone by means of a flexible tubular acoustic member. A battery powered amplifier and filter circuit is provided within the component case and the amplified and filtered output of the microphone is coupled to a miniature speaker sealed within an airtight container within the case. A rotatable tubular member having radial apertures therein is coupled through the sealed container and out each side of the component case. A binaural headpiece is acoustically coupled to each end of the rotatable member and is thus free to rotate with respect to the case, allowing the stethoscope to fold for storage. In a preferred embodiment of the present invention, electronic timing means are provided for automatically removing electrical power from the amplifier circuit after a predetermined period of time and for generating an audible tone at preselected intervals for pulse rate measurement.

BRIEF DESCRIPTION OF THE DRAWINGS

The novel features believed characteristic of the invention are set forth in the appended claims. The invention itself; however, as well as a preferred mode of use, further objects and advantages thereof, will best be understood by reference to the following detailed description of an illustrative embodiment when read in conjunction with the accompanying drawings, wherein:

DETAILED DESCRIPTION OF THE PREFERRED EMBODIMENT

Figure 1:
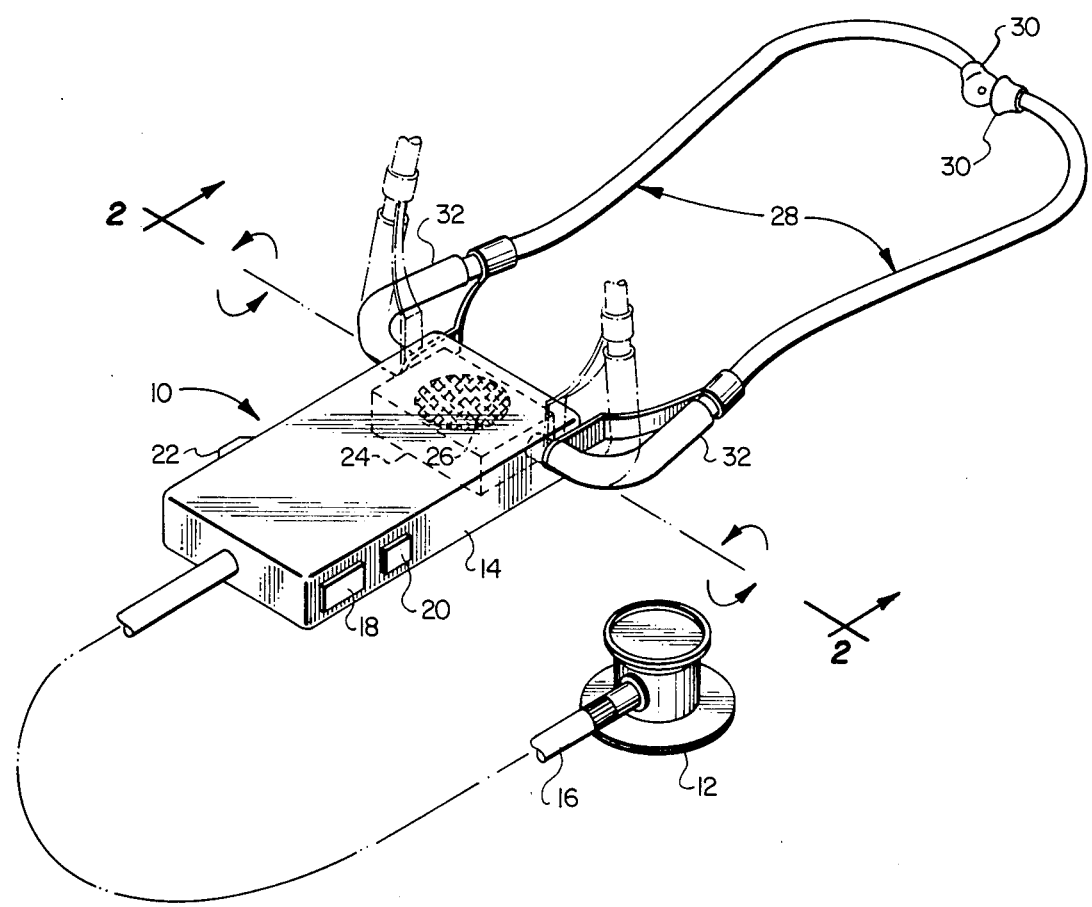
FIG. 1 is a perspective view of the novel electronic stethoscope of the present invention.

Referring now to the figures and in particular with reference to FIG. 1, there is depicted a perspective view of electronic stethoscope 10 of the present invention. As can be seen, stethoscope 10 includes a standard acoustic pickup head 12 which is coupled to an electronic component case 14 by means of a flexible tubular acoustic member 16. Electronic component case 14 is preferably constructed of plastic material such as polystyrene and includes an "on" switch 18, an "off" switch 20; and a slidable volume switch 22 which is disposed on the opposite side of electronic component case 14 from switches 18 and 20. Further, electronic component case 14 is preferably palm sized, or approximately three inches in width so that an individual may operate switches 18 and 20 with his fingertips while simultaneously adjusting volume switch 22 with his thumb. This particular switch configuration and case size are important features of electronic stethoscope 10 and contribute greatly to the ease of operation of this device.

Depicted within electronic component case 14 is rotatable acoustic coupling section 24 which serves to mount speaker 26 in a manner which will be explained in detail below. The output of acoustic coupling section 24 is rotatably coupled to binaural headpiece 28 utilizing flexible tubes 32. This rotatable coupling of binaural headpiece 28 is an important feature of electronic stethoscope 10 and permits electronic stethoscope to be folded and stored in the same manner as an acoustic stethoscope, as depicted in phantom lines within FIG. 1.

Binaural headpiece 28 also includes silicon rubber earpieces 30 which will maximize wearer comfort during use of electronic stethoscope 10.

Figure 2:
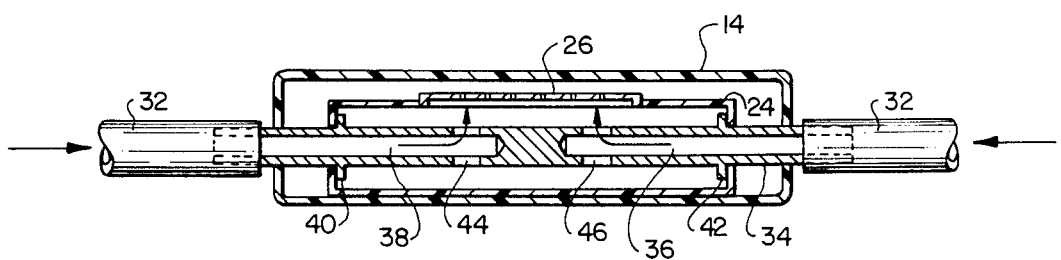
FIG. 2 is a sectional view of the novel rotatable acoustic coupling section of the electronic stethoscope of the present invention.

Referring now to FIG. 2, there is depicted a sectional view of rotatable acoustic coupling section 24 of electronic stethoscope 10. As can be seen in FIGS. 1 and 2, acoustic coupling section 24 comprises a rectangular sealed container which is preferably airtight and which is also constructed of plastic materials similar to electronic component case 14. An aperture in the upper surface of acoustic coupling section 24 is utilized to receive and sealably mount speaker 26. Speaker 26 is preferably a high efficiency acoustic speaker, the output of which is directed into the interior of acoustic coupling section 24. Thus, any acoustic signals coupled to speaker 26 will be audibly generated within the confines of acoustic coupling section 24.

Mounted through acoustic coupling section 24 and extending out through each side of electronic component case 14 is a rotatable tubular member 34 width serves to couple the acoustic signals within acoustic coupling section 24 out to binaural headpiece 28 by means of flexible tubes 32. In a preferred embodiment of the present invention, rotatable tubular member 34 is a metallic cylinder which includes axial bores 36 and 38 which extend into the interior of acoustic coupling section 24. Additionally, flanges 40 and 42 are provided to seal the point at which rotatable tubular member 34 penetrates acoustic coupling section 24. Those ordinarily skilled in the art will appreciate that o-rings or other sealing means may also be utilized to provide sealing at the point of penetration with acoustic coupling section 24.

As can be seen in FIG. 2, axial bores 36 and 38 are penetrated by radial apertures 44 and 46 in the vicinity of speaker 26 and thus permit the acoustic signals within acoustic coupling section 24 to enter axial bores 36 and 38 and be acoustically coupled out of acoustic coupling section 24 through axial bores 36 and 38 and into flexible tubes 32. Radial apertures 44 and 46 represent an important feature of the acoustic coupling section of electronic stethoscope 10 and are preferably situated at an angle which maximizes acoustic coupling from speaker 26 when binaural headpiece 28 rotated into the position depicted in FIG. 1, for utilization of electronic stethoscope 10 in a practical manner.

Figure 3:
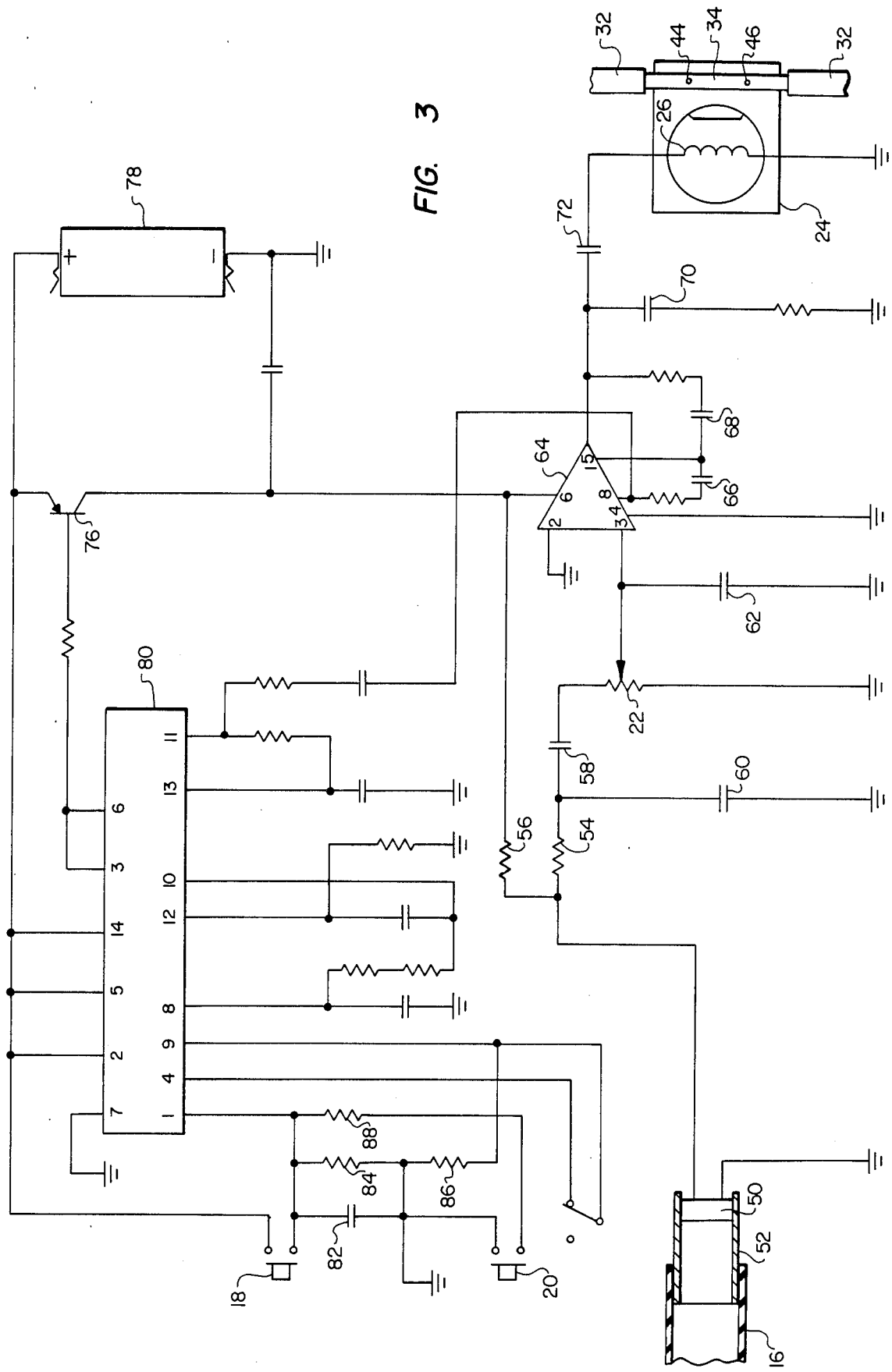
FIG. 3 is a schematic diagram of the electronic circuitry of the electronic stethoscope of the present invention.

With reference now to FIG. 3, there is depicted a schematic diagram of the electronic circuitry of electronic stethoscope of the present invention. Where possible, the reference numerals utilized in FIGS. 1 and 2 have been utilized to identify the same components depicted in schematic form in FIG. 3. As can be seen, flexible tubular acoustic member 16 couples pickup head 12 (not shown) to electronic microphone 50 via a push fit connector 52. The output of microphone 50 is then coupled via resistors 54 and 56 and capacitor 58 to potentiometer 22.

The signal applied to potentiometer 22, minus high frequencies filtered out by capacitors 60 and 62, is then coupled to the input of amplifier 64 for amplification and filtering by means of capacitors 66 and 68 in a feedback loop. Final filtering is accomplished by capacitors 70 and 72 and the effect of the entire filter network is to enhance the frequency band between twenty and seven hundred hertz before applying the amplified and filtered output of microphone 50 to speaker 26 within acoustic coupling section 24. In this manner any spurious high frequency transmissions originating in fluorescent fixtures or the like will be filtered out of the resultant signal.

Electrical power is applied to amplifier 64 by means of a gate controlled conduction device 76, a PNP transistor, which is coupled between battery 78 and pin 6 of amplifier 64. The bias present on the base of transistor 76, and thus the conduction of electrical power to amplifier 64, is controlled by timing and control circuit 80.

In a preferred embodiment of the present invention, timing and control circuit 80 is implemented utilizing a quad two-input NAND gate integrated circuit device such as the CD4093 manufactured by National Semiconductor of Santa Clara, Calif. Timing and control circuit 80 is utilized for four separate timing or control outputs in a highly efficient and novel manner. One function of timing and control circuit 80 is to provide an automatic removal of electrical power from amplifier 64 after the elapse of a selected period of time. Power is applied to amplifier 64 by a momentary depression of "on" switch 18 which causes capacitor 82 to charge to battery potential. The voltage present on capacitor 82 is then coupled to pin 1 of timing and control circuit 80 and together with the battery potential at pin 2 will cause an output at pin 3 which will turn on transistor 76.

Automatic power removal is accomplished by allowing capacitor 82 to slowly discharge through resistor 84 until such time as the voltage present drops below the level necessary to provide the desired input at pin 1. At that time, transistor 76 will cease conduction and electrical power will be removed from amplifier 64. In a preferred mode of this invention, this period of time should be between two and three minutes to minimize possible battery drain due to inadvertent failure to depress the "off" switch. Those skilled in this art will appreciate that a manual depression of "off" switch 20 can be utilized to cause a rapid discharge of capacitor 82 through the much smaller resistance of resistor 88.

In a similar manner, switch 90 can be utilized to generate a periodic signal in the audible range at pin 11 of timing and control circuit 80. This audible signal or tone is coupled to pin 8 of amplifier 64 and superimposed on the output thereof to provide a calibrated timing tone for pulse rate measurements. The resistive and capacitive elements coupled to pins 8, 12, 10, 13 and 11 of timing and control circuit 80 are utilized, in a manner well known in the art, to select the frequency of the timing tone, the duration of that tone and the duration between consecutive tones. Preferably, a short tone is sounded every fifteen seconds when switch 90 is closed to enable a simple pulse rate calibration for pulse beats per minute.

As can be seen, the electronic circuitry of FIG. 3 is a highly efficient utilization with a minimum amount of electronic components and can be easily mounted on a printed circuit board within electronic component case 14.

Although the invention has been described with reference to a specific embodiment, this description is not meant to be construed in a limiting sense. Various modifications of the disclosed embodiment as well as alternative embodiments of the invention will become apparent to persons skilled in the art upon reference to the description of the invention. It is therefore contemplated that the appended claims will cover any such modifications or embodiments that fall within the true scope of the invention.

What is claimed is:

1. An electronic stethoscope comprising:

an electronic component case for encompassing electronic components in circuitry;
a pickup head;
a microphone;
a first tubular acoustic member coupling said pickup head and said microphone;
a binaural headpiece;
a speaker mounted within said electronic component case;
an amplifier circuit having its input coupled to said microphone and its output coupled to said speaker;
a rotatable tubular member disposed adjacent to said speaker and extending out through each side of said electronic component case for coupling the output of said speaker out of said electronic component case; and
means coupling said binaural headpiece to said rotatable tubular member whereby said binaural headpiece may be rotated with respect to said electronic component case for ease in storage of said electronic stethoscope.

2. The electronic stethoscope according to claim 1 further including switch means for applying electrical power to said amplifier circuit in response to operation thereof.

3. The electronic stethoscope according to claim 1 further including timer means for removing electrical power from said amplifier circuit after a predetermined period of time has elapsed.

4. The electronic stethoscope according to claim 1 wherein said rotatable tubular member comprises a hollow metallic cylinder having radial apertures in the body thereof.

5. The electronic stethoscope according to claim 1 wherein said electronic component case is rectangular in shape.

6. An electronic stethoscope according to claim 1 wherein said electronic component case includes a first switch means for applying electric power to said amplifier circuit in response to operation thereof and said second switch means for varying the amplification of said amplifier circuit said first and second switch means disposed on opposing sides of said case whereby said first and second switch means may be operated by the thumb and fingers of an individual grasping said case.

7. The electronic stethoscope according to claim 6 wherein said second switch means comprises a slide switch.

8. The electronic stethoscope according to claim 6 further including a third switch means for removing electrical power from said amplifier circuit in response to operation thereof, said third switch means disposed adjacent to said first switch means for finger control.

* * * * *